United States Patent [19]

Kawashima et al.

[11] Patent Number: 4,699,007
[45] Date of Patent: Oct. 13, 1987

[54] METHOD OF AND APPARATUS FOR ULTRASONIC FLAW DETECTION

[75] Inventors: Sadao Kawashima, Kobe; Yoshikazu Mori, Nishinomiya; Masayoshi Iwasaki, Miki; Norio Suzuki, Kobe, all of Japan

[73] Assignee: Kabushiki Kaisha Kobe Seiko Sho, Kobe, Japan

[21] Appl. No.: 752,596

[22] Filed: Jul. 8, 1985

[30] Foreign Application Priority Data

Jul. 13, 1984 [JP] Japan ............... 59-146488
Nov. 19, 1984 [JP] Japan ............... 59-245369
Mar. 4, 1985 [JP] Japan ............... 60-43038

[51] Int. Cl.$^4$ ............................................ G01N 29/04
[52] U.S. Cl. ............................... 73/622; 73/625; 73/641
[58] Field of Search .............. 73/622, 625, 628, 637, 73/641, 626, 602, 599, 589, 658, 624

[56] References Cited

U.S. PATENT DOCUMENTS

| 3,321,959 | 5/1967  | Wood et al. ............. 73/622 |
| 3,332,278 | 7/1967  | Wood et al. ............. 73/602 |
| 3,552,191 | 1/1971  | Heseding ................ 73/624 |
| 3,981,184 | 9/1976  | Matay ................... 73/622 |
| 4,412,451 | 11/1983 | Uusitalo et al. ......... 73/599 |
| 4,523,468 | 6/1985  | Derkacs et al. .......... 73/622 |
| 4,542,644 | 9/1985  | Claytor et al. .......... 73/599 |
| 4,567,747 | 2/1986  | Matay ................... 73/622 |

Primary Examiner—Anthony V. Ciarlante
Attorney, Agent, or Firm—Oblon, Fisher, Spivak, McClelland & Maier

[57] ABSTRACT

A plurality of ultrasonic transducers or probes are positioned around a region of an object such as a steel tube to be inspected. One of the ultrasonic transducers is energized to emit an ultrasonic beam into the region, and ultrasonic waves reflected from and transmitted through the region in response to the emitted ultrasonic beam are received. Sound pressures are then measured from the reflected and transmitted ultrasonic waves, and an evaluation value is produced by arithmetically dividing the sound pressure of the reflected ultrasonic wave by the sound pressure of the transmitted ultrasonic wave.

6 Claims, 18 Drawing Figures

METHOD OF AND APPARATUS FOR ULTRASONIC FLAW DETECTION

BACKGROUND OF THE INVENTION

The present invention relates to a nondestructive method of and apparatus for ultrasonically detecting flaws which are produced with time in solid objects such for example as steel tubes manufactured by a centrifugal casting process.

Heating tubes for use in reforming a gas in contact with water vapor comprise heat-resistant cast tubes made of austenite steel such as HK-40 (including 0.40% of carbon, 25% of chromium, and 20% of nickel) and manufactured primarily by centrifugal casting for increased resistance against corrosion, heat, and pressure. A plurality of such cast tubes are welded together to provide a prescribed tube length. In use, steam and a raw material gas are fed under pressure into the tube filled with a catalyst, and the tube is heated to a high temperature by an external heater. Since the tube is subject to high temperature and pressure, it tends to develop, in about three years, time-dependent fissures caused by thermal stresses due to the temperature difference between the heated outer surface and the cool inner surface of the tube or defects in the inner surface of the tube due to such temperature difference. It is highly important for stable operation and safety of the tube to detect such time-dependent flaws in a nondestructive manner for accurately grasping the remaining service life of the tube.

Nondestructive testing methods for checking flaws in tubes manufactured by centrifugal casting include radiographic inspection and ultrasonic flaw detection.

The radiographic inspection method is effective to detect flaws which have certain dimensions in the direction in which the radiation is transmitted. The flaws can effectively be detected if they have a thickness of 1% or more of the wall thickness of an object being inspected and extend in a direction normal to the direction of travel of the radiation. Other defects such as cracks cannot be detected by the radiographic method. Therefore, the radiographic inspection process is low in its detecting accuracy.

The ultrasonic flaw detection is highly effective in inspecting internal flaws in relatively homogenenous steel materials such as general wrought steel and cast carbon steel. Various methods are known for ultrasonic flaw detection. For example, they include a reflection method, a through transmission method, and a resonance method. Some ultrasonic flaw detecting processes employ one or two ultrasonic probes, or emit an ultrasonic wave perpendicularly or obliquely to an object to be tested. These different inspection methods are selected dependent on the shape of the object, the type of flaws in the object, and other factors.

With the heat-resistant tube made of austenite steel by centrifugal casting, however, difficulty has been experienced in detecting any flaws therein since the tube material causes the ultrasonic energy to be dampened therein to a large extent and the displayed image is rendered complex by many echo pulses as large crystals cause grain boundary reflection. Another problem is that it is difficult to transmit a required amount of ultrasonic energy through the tube because of the casting surface on the outer tube surface. Therefore, the ultrasonic flaw detecting method has not extensively been relied upon for detecting defects in heat-resistant tubes of austenite cast steel since the ultrasonic flaw detection has a low rate of detecting defects in such tubes.

Japanese unexamined Patent Publication No. Sho 58-47252 discloses a technique for detecting flaws in a circumferential welded tube portion by measuring an ultrasonic energy having transmitted through the welded seam and opposite tube portions adjacent to the welded seam, and adding and substracting the three measured values according to evaluation equations to ascertain whether there is a defect or not. This flaw detecting technique however still has a low detecting accuracy since the material properties differ in the measured points and such property differences affect the noise level, and the three measuring points are not always selected with good accuracy. Japanese unexamined Patent Publication No. Sho 59-99251 shows the use of three ultrasonic probes which however suffer from the same drawbacks as mentioned above.

The applicant has filed Japanese Patent Application No. 59-146488 on a method of compensating for differences in the attenuation coefficient of the material. The disclosed method is however incapable of removing the problem of dispersion of the ultrasonic energy due to varying transmission and reception efficiencies of individual probes, different patterns (spreading patterns) of ultrasonic beams, and different material properties in beam paths.

SUMMARY OF THE INVENTION

It is an object of the present invention to provide a method of ultrasonically detecting a flaw in a solid object made of anisotropic austenite stainless steel of coarse crystal grain wtih a plurality of ultrasonic probes by using a constant threshold level, without being adversely affected by various different properties such as different transmission, reception efficiencies of the probes, different incident and outgoing efficiencies thereof, varying ultrasonic beam patterns, and varying material properties in beam paths.

Another object of the present invention is to provide an apparatus for carrying out the above method.

According to the present invention, a plurality of ultrasonic transducers are positioned around a region of an object to be inspected, one of the ultrasonic transducers is energized to emit an ultrasonic beam into the region, and ultrasonic waves reflected from and transmitted through the region in response to the emitted ultrasonic beam are received. Sound pressures are then measured from the reflected and transmitted ultrasonic waves, and an evaluation value is produced by arithmetically dividing the sound pressure of the reflected ultrasonic wave by the sound pressure of the transmitted ultrasonic wave.

In one preferred embodiment of the present invention, four ultrasonic transducers are disposed around the region in angularly spaced relation to each other, the four ultrasonic transducers being sequentially energized to emit ultrasonic beams, and two of the four ultrasonic transducers which are adjacent and diagonally opposite to the energized ultrasonic transducer being sequentially selected to receive the reflected and transmitted ultrasonic waves, repectively.

In another embodiment, two ultrasonic transducers are disposed one on each side of the region, the two ultrasonic transducers being alternately energized to emit ultrasonic beams and simultaneously operated to receive the reflected and transmitted ultrasonic waves, respectively.

According to still another embodiment, four ultrasonic transducers are disposed around the region in angularly spaced relation to each other, two of the four ultrasonic transducers being alternately energized to emit ultrasonic beams, and the other two of the four ultrasonic transducers which are adjacent and diagonally opposite to the energized ultrasonic transducer being selected to receive the reflected and transmitted ultrasonic waves, respectively.

According to a still further embodiment, three ultrasonic transducers are disposed around the region in angularly spaced relation to each other, two of the three ultrasonic transducers other than the one ultrasonic transducer being simultaneously operated to receive the reflected and transmitted ultrasonic waves, respectively.

The method of the present invention can be carried out by an apparatus for ultrasonically detecting a flaw in an object, comprising a plurality of ultrasonic transducers disposed movably with respect to the object for sequentially emitting ultrasonic waves to a region of the object to be inspected and for receiving ultrasonic waves reflected from and transmitted through the region and converting the received ultrasonic waves to electric signals, an encoder for generating a positional signal indicating the position of the ultrasonic transducers with respect to the object, means responsive to the positional signal for sequentially energizing the ultrasonic transducers and receiving the electric signals from the ultrasonic transducers, an analog-to-digital converter for converting the received electric signals to digital signals, a register for storing the digital signals, and a computer for processing the digital signals from the register into an evaluation value by arithmetically dividing the sound pressure of the reflected ultrasonic wave by the sound pressure of the transmitted ultrasonic wave.

The aforesaid means comprises a channel selector for sequentially selecting one of the ultrasonic transducers as an ultrasonic transmitter for emitting the ultrasonic wave and two of the ultrasonic transducers as ultrasonic receivers for receiving the reflected and transmitted ultrasonic waves, and an ultrasonic tester for energizing the selected ultrasonic transmitter and receiving the electric signals from the selected ultrasonic receivers.

The above and other objects, features and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
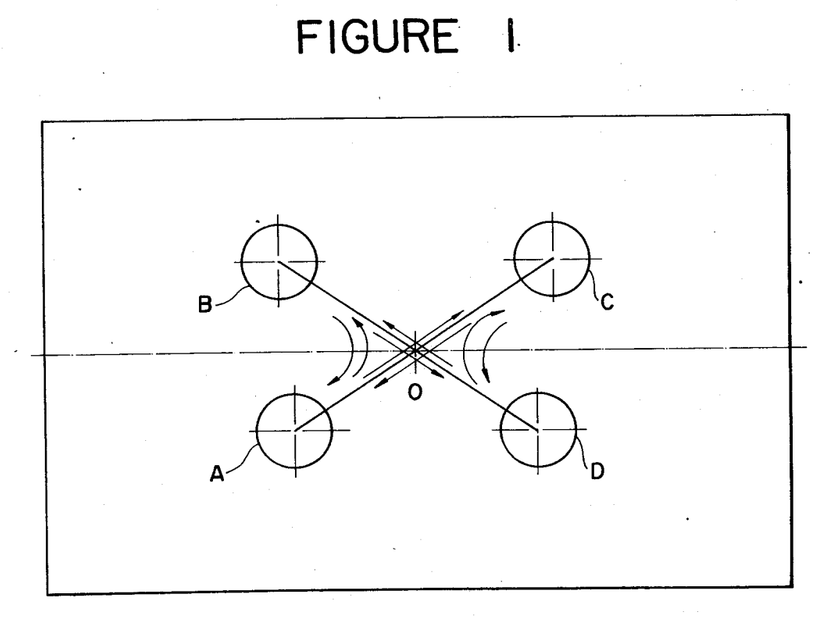
FIG. 1 is a veiw showing an arrangement of four ultrasonic probes employed in a method according to an embodiment of the present invention.

An ultrasonic flaw detecting method according to the present invention will be described with reference to FIG. 1. In FIG. 1, the ultrasonic flaw detecting method is effected on a heating tube made of austenite heat-resistant cast steel. However, the present invention is also applicable to the inspection of sheets for defects therein or tubes and sheets made of materials which produce high noise levels due to grain boundaries.

As illustrated in FIG. 1, four ultrasonic probes or transducers A, B, C, D are disposed around a tube 1 to be inspected. The ultrasonic porbes A, B, C, D are positioned so that ultrasonic waves generated thereby are transmitted through the tube 1 in axial and circumferential directions and reflected by an internal defect O extending circumferentially in the tube 1. More specifically, when one of the probes A is energized to transmit an ultrasonic beam, the probe B receives an ultrasonic echo reflected by the defect O and the probe C receive an ultrasonic beam having passed through the defect O. When the other probes B, C, D are energized to transmit respective ultrasonic beams, the probe combinations A and D, D and A, C and B similarly serve as ultrasonic receivers for receiving reflected and transmitted ultrasonic energies. The beam paths in the tube 1 are indicated by the arrows in FIG. 1.

The four probes A, B, C, D are sequentially energized to act as ultrasonic transmitters for transmitting ultrasonic beams, and the corresponding probe pairs are sequentially employed to receive reflected and transmitted ultrasonic waves.

As a result of the above sequential ultrasonic trasnmission and reception process, the four probes A, B, C, D sequentially measure four reflected ultrasonic energies or sound pressures PAB, PBA, PCD, PDC and four transmitted ulrasonic energies or sound pressures PAC, PCA, PDB, PBD.

The recieved sound pressures are expressed as follows:

Reflected:
$PAB = PA \cdot \zeta A \cdot \xi AO \cdot \delta AB \cdot \xi OB \cdot \eta B$
$PBA = PB \cdot \zeta B \cdot \xi BO \cdot \delta BA \cdot \xi OA \cdot \eta A$
$PCD = PC \cdot \zeta C \cdot \xi CO \cdot \delta CD \cdot \xi OD \cdot \eta D$
$PDC = PD \cdot \zeta D \cdot \xi DO \cdot \delta DC \cdot \xi OC \cdot \eta C$
Transmitted:

$PAC = PA \cdot \zeta A \cdot \xi AO \cdot \gamma AC \cdot \xi OC \cdot \eta C$
$PCA = PC \cdot \zeta C \cdot \xi CO \cdot \ominus CA \cdot \xi OA \cdot \eta A$
$PDB = PD \cdot \zeta D \cdot \xi DO \cdot \gamma DB \cdot \xi OB \cdot \eta B$
$PBD = PB \cdot \zeta B \cdot \xi BO \cdot \gamma BD \cdot \xi OD \cdot \eta D$ where PAB (PBA, PCD, PDC, PAC, PCA, PDB, PBD): the sound pressure when the ultrasonic wave transmitted by the probe A (B, C, D, A, C, D, B) is received by the probe B (A, D, C, D, A, B, D);

PA (PB, PC, PD): the sound pressure transmitted by the probe A (B, C, D);

$\zeta A$ ($\zeta B$, $\zeta C$, $\zeta D$): the transmission efficiency (including the incident efficiency at the tube surface) of the probe A (B, C, D);

$\xi AO$ ($\xi BO$, $\xi CO$, $\xi DO$, $\xi DA$, $\xi OB$, $\xi DC$, $\xi OD$): all of the influencing factors such as ultrasonic dispersion by crystals based on the patterns and lengths of beams in beam paths from the probe A (or defect) (B, C, D, D, O, D, O) to the defect O (or probe) (O, O, O, A, B, C, D), and different material properties;

$\delta AB$ ($\delta BA$, $\delta CD$, $\delta DC$): the reflection coefficient of the defect wih respect to the beam from the probe A (B, C, D) to the probe B (A, D, C);

$\gamma AC$ ($\gamma CA$, $\gamma DB$, $\gamma BD$): the transmittion coefficient of the defect with resepct to the beam from the probe A (C, C, B) to the probe C (A, B, D); and $\eta A$ ($\eta B$, $\eta C$, $\eta D$): the reception efficiency of the probe A (B, C, D) (including the outgoing efficiency at the tube surface).

The product of the four reflected sound pressures are divided by the product of the four transmitted sound pressures as follows:

$$\frac{\text{Product of reflected sound pressures}}{\text{Product of transmitted sound pressures}}$$

$$= \frac{PAB \times PBA \times PCD \times PDC}{PAC \times PCA \times PDB \times PBD}$$

$$= \frac{\delta AB \times \delta BA \times \delta CD \times \delta DC}{\gamma AC \times \gamma CA \times \gamma DB \times \gamma BD}$$

= a constant dependent solely on the shape of the defect $= K_C^4$

The above arithmetic operation was confirmed by an experiment. A tube having an outside diameter of 123 mm, an inside diameter of 83.6 mm and a wall thickness of 19.7 mm with a defect having a depth which is ½ of the wall thickness of the tube and extending over 20 mm in the circumferential direction was inspected by the ultrasonic probes arranged as shown in FIG. 1 and energized to produce ultrasonic waves having a frequency of 1 MHz. The results are illustrated in FIGS. 2a through 2h.

Figure 2A:
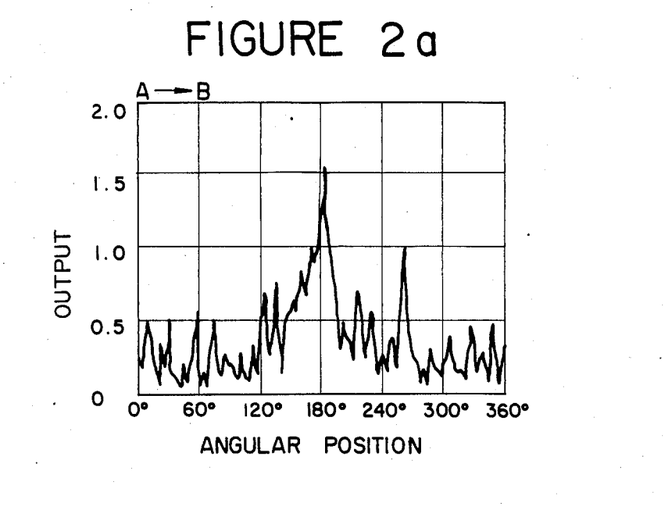
FIGS. 2a through 2h are graphs showing the waveforms of reflected and transmitted ultrasonic energies between different probe pairs, dependent on the angular position around a tube being inspected.
Figure 2B:
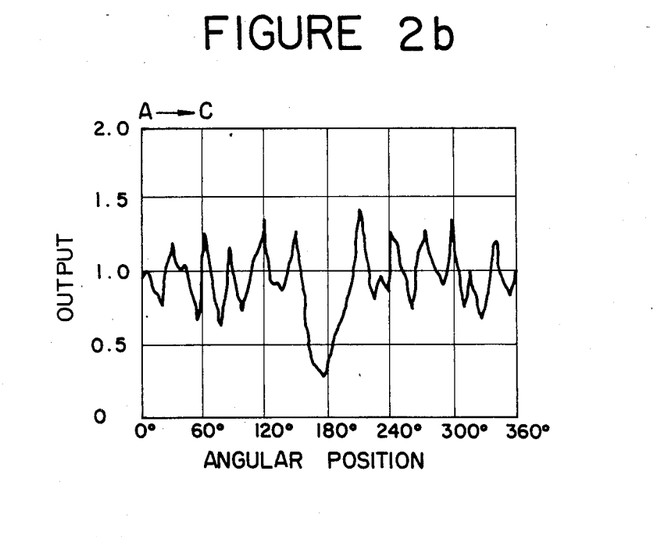
Figure 2C:
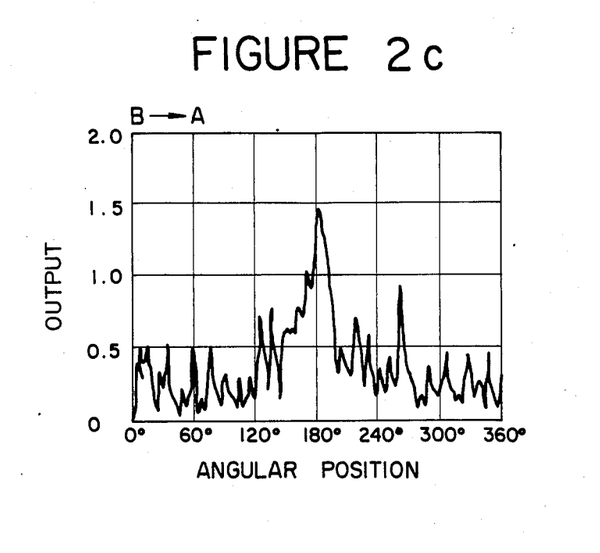
Figure 2D:
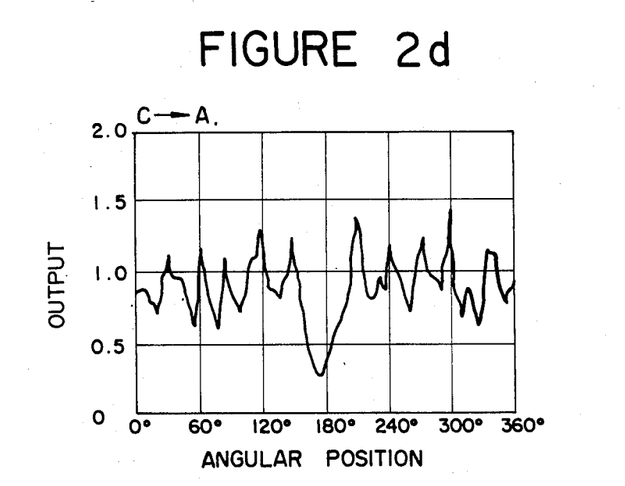
Figure 2E:
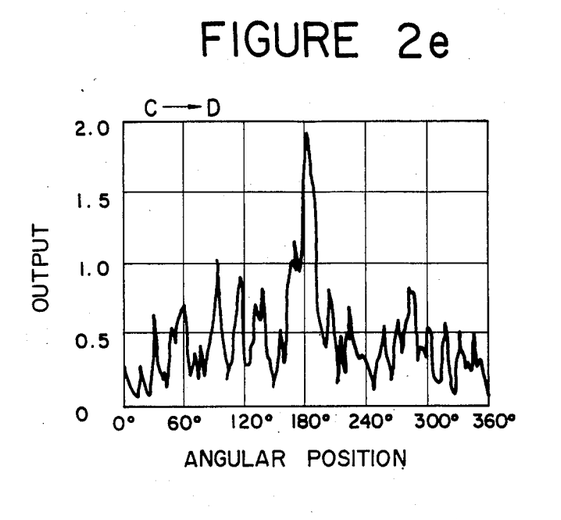
Figure 2F:
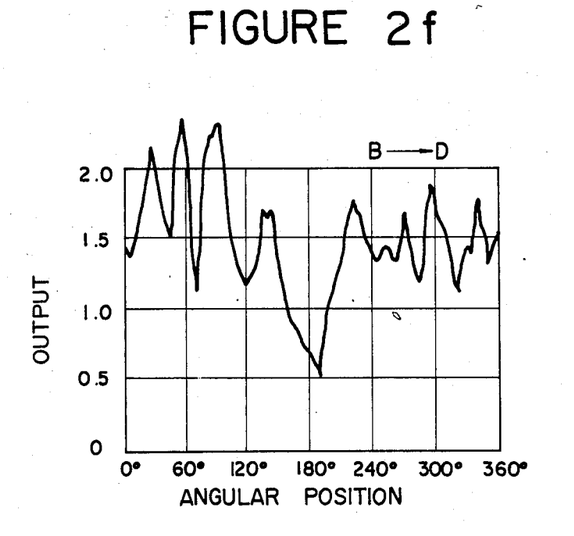
Figure 2G:
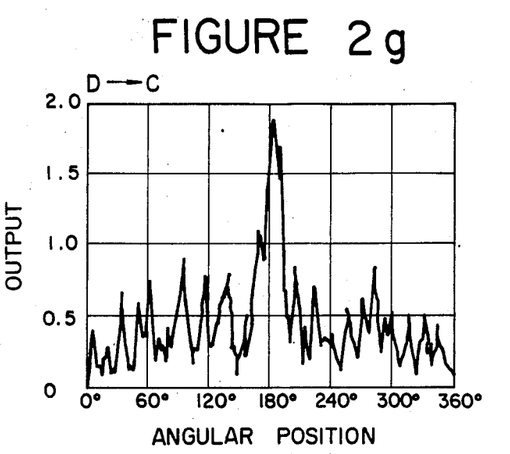
Figure 2H:
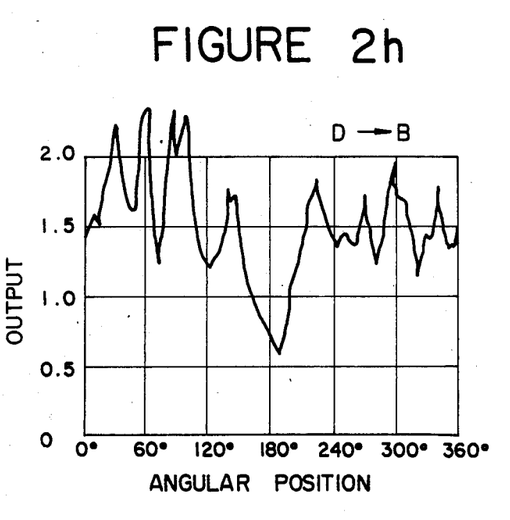

The graph shown in each of FIGS. 2a through 2h has a horizontal axis indicating the angular position around the tube and a vertical axis representing the received sound pressure. FIG. 2a shows the sound pressure produced when the ultrasonic wave emitted from the probe A was reflected by the defect and received by the probe B. FIG. 2b shows the sound pressure produced when the ultrasonic wave emitted from the probe A was transmitted through the defect and received by the probe C. FIG. 2c shows the sound pressure produced when the ultrasonic wave emitted from the probe B was reflected by the defect and received by the probe A. FIG. 2d shows the sound pressure produced when the ultrasonic wave emitted from the probe C was transmitted through the defect and received by the probe A. FIG. 2e shows the sound pressure produced when the ultrasonic wave emitted from the probe C was reflected by the defect and received by the probe D. FIG. 2f shows the sound pressure produced when the ultrasonic wave emitted from the probe B was transmitted through the defect and received by the probe D. FIG. 2g shows the sound pressure produced when the ultrasonic wave emitted from the probe D was reflected by the defect and received by the probe C. FIG. 2h shows the sound pressure produced when the ultrasonic wave emitted from the probe D was transmitted through the defect and received by the probe B. In the actual inspection process, the probes A, B, C, D were moved around the tube while at the same time they were switched, with a resulting positional error equal to a few m sec. which was negligible in view of the spreading of the beams.

Figure 3:
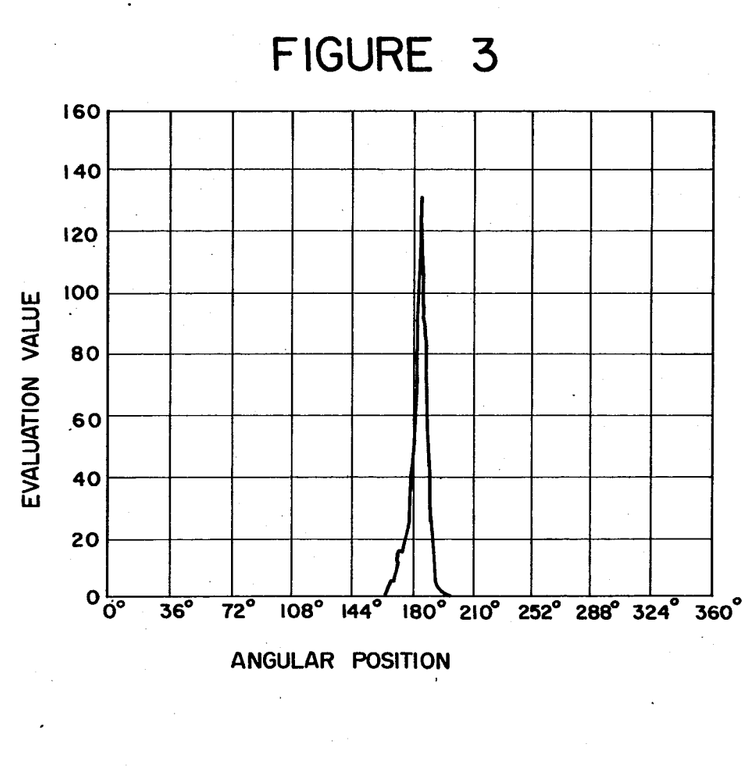
FIG. 3 is a graph illustrating a waveform produced from the waveforms of FIGS. 2a through 2h according to an arithmetic operation.

FIG. 3 shows a result obtained by subjecting the measured data to the arithmetic operation according to the present invention. In FIG. 3, the signals received from other than the defect O are random noises such as scattered echoes from grain boundaries in the beam paths, and are smoothed out by the arithmetic operation, resulting in a reduced sound pressure. By effecting the above arithmetic operation, therefore, the noises are reduced and the the signals from the defect are emphasized, so that S/N ratio is improved.

The present invention is not limited to the above method of detecting flaws in the heating tube of austenite heat-resistant cast steel, but may be applicable to methods of detecting flaws in various shaped and materials such as cast masses and thin sheets having different localized areas which attenuate ultrasonic waves, and different crystal grain sizes, directions and shapes.

While in the above embodiment the defect O is oriented in the circumferential direction of the tube, a defect lying in the axial direction of the tube may be detected by the same probe arrangement as shown in FIG. 1. In operation, however, when the probe A is an ultrasonic transmitter, for example, then the probe D serves as an ultrasonic receiver for receiving an ultrasonic echo from the axial defect. The received sound pressures are expressed as follows:

Reflected:
$PAD = PA \cdot \zeta A \cdot \xi AO \cdot \delta AD \cdot \xi OD \cdot \eta D$
$PBC = PB \cdot \zeta B \cdot \xi BO \cdot \delta BC \cdot \xi OC \cdot \eta C$
$PCB = PC \cdot \zeta C \cdot \xi CO \cdot \delta CB \cdot \xi OB \cdot \eta B$
$PDA = PD \cdot \zeta D \cdot \xi DO \cdot \delta DA \cdot \xi OA \cdot \eta A$ Transmitted:
$PAC = PA \cdot \zeta A \cdot \xi AO \cdot \gamma AC \cdot \xi OC \cdot \eta C$
$PCA = PC \cdot \zeta C \cdot \xi CO \cdot \gamma CA \cdot \xi OA \cdot \eta A$
$PDB = PD \cdot \zeta D \cdot \xi DO \cdot \gamma DB \cdot \xi OB \cdot \eta B$
$PBD = PB \cdot \zeta B \cdot \xi BO \cdot \gamma BD \cdot \xi OD \cdot \eta D$ Therefore, $$\frac{\text{Product of reflected sound pressures}}{\text{Product of transmitted sound pressures}}$$

$$= \frac{PAD \times PBC \times PCB \times PDA}{PAC \times PBD \times PCA \times PDB}$$

$$= \frac{\delta AD \times \delta BC \times \delta CB \times \delta DA}{\gamma AC \times \gamma BD \times \gamma CA \times \gamma DB}$$

= a constant dependent solely on the shape of the defect $= K_R^4$

Figure 4:
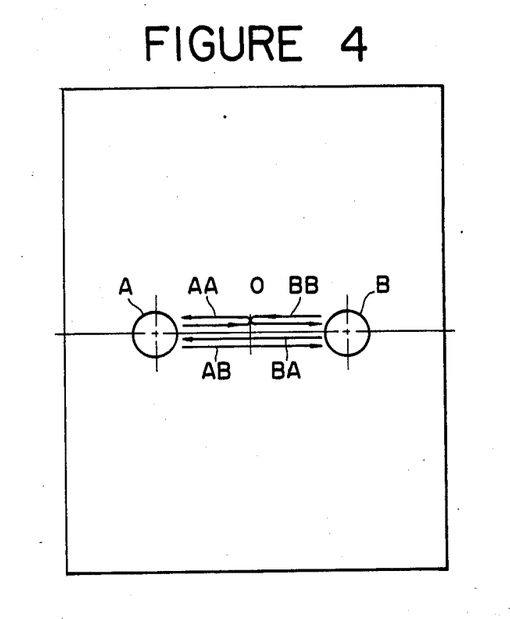
FIG. 4 is a view of an arrangement of two ultrasonic probes employed in a method according to another embodiment of the present invention.

FIG. 4 shows an ultrasonic flaw detecting method according to another embodiment of the present invention. This ultrasonic detecting method is utilized where a defect O is oriented in a fixed direction in an object 1 such as a tube. Two ultrasonic probes or transducers A, B are disposed one on each side of the defect O in sandwiching relation in a direction normal thereto. In operation, the probe A is energized as an ultrasonic transmitter for emitting an ultrasonic beam toward the probe B which receives an ultrasonic wave transmitted through the defect O. Alternatively, the probe A is employed as an ultrasonic transmitter/receiver for emitting an ultrsonic beam toward the probe B. The probe A then receives an ultrasonic echo reflected from the defect O in a beam path AA, and the probe B receives an ultrasonic wave transmitted through the defect O in a beam path AB.

Then, the probe B is energized as an ultrasonic transmitter for emitting an ultrasonic beam toward the probe A which receives an ultrasonic wave transmitted through the defect O. Alternatively, the probe B is employed as an ultrasonic transmitter/receiver for emitting an ultrsonic beam toward the probe A. The probe B then receives an ultrasonic echo reflected from the defect O in a beam path BB, and the probe B receives an ultrasonic wave transmitted through the defect O in a beam path BA.

In the foregoing alternate ultrasonic trasnmission and reception process, the two probes A, B alternately measure two reflected ultrasonic energies or sound pressures PAA, PBB and two transmitted ultrasonic energies or sound pressures PAB, PBA.

The received sound pressures are expressed as follows:

Reflected:
$PAA = PA \cdot \zeta A \cdot \xi AO \cdot \delta AA \cdot \xi OA \cdot \eta A$
$PBB = PB \cdot \zeta B \cdot \xi BO \cdot \delta BB \cdot \xi OB \cdot \eta B$
Transmitted:
$PAB = PA \cdot \zeta A \cdot \xi AO \cdot \gamma AB \cdot \xi OB \cdot \eta B$
$PBA = PB \cdot \zeta B \cdot \xi BO \cdot \gamma BA \cdot \xi OA \cdot \eta A$ where
PAA (PBB, PAB, PBA): the sound pressure when the ultrasonic wave transmitted by the probe A (B, A, B) is received by the probe A (B, B, A);
PA (PB): the sound pressure transmitted by the probe A (B);
$\zeta A$ ($\zeta B$): the transmission efficiency (including the incident efficiency at the tube surface) of the probe A (B);
$\xi AO$ ($\xi BO$, $\xi OA$, $\xi OB$): all of the influencing factors such as ultrasonic dispersion by crystals based on the profiles and lengths of beams in beam paths from the probe A (or defect) (B, O, O) to the defect O (or probe) (O, A, B), and different material properties;
$\delta AA$ ($\delta BB$): the reflection coefficient of the defect with respect to the beam from the probe A (B) to the probe A (B);
$\gamma AB$ ($\gamma BA$): the transmition coefficient of the defect with respect to the beam from the probe A (B) to the probe B (A); and
$\eta A$ ($\eta B$): the reception efficiency of the probe A (B) (including the outgoing efficiency at the tube surface).

The product of the two reflected sound pressures are divided by the product of the two transmitted sound pressures as follows:

$$\frac{\text{Product of reflected sound pressures}}{\text{Product of transmitted sound pressures}}$$

$$= \frac{PAA \times PBB}{PAB \times PBA} = \frac{\delta AA \times \delta BB}{\gamma AB \times \gamma BA}$$

= a constant dependent solely on the shape of the defect $= K^2$

Whether there is a defect or not can be determined with a constant threshold at all times from the result computed by the above arithmetic operation.

The computed value should preferably be extracted by the power equal to the number of terms multiplied to produce an evaluation value K in which the output level is adjusted for easier evaluation of the result.

Figure 5:
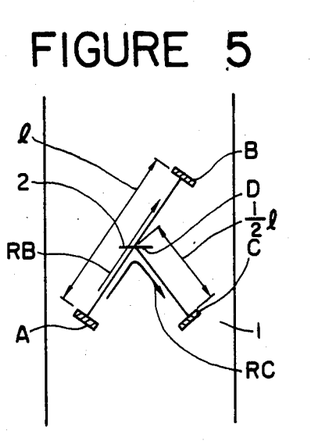
FIG. 5 is a view of an arrangement of three ultrasonic probes utilized in a method of still another embodiment.

FIG. 5 is explanatory of an ultrasonic flaw detecting method according to still another embodiment of the present invention. When all of the influencing factors such as, ultrasonic dispersion by crystals based on the profiles and lengths of beams in beam paths and material properties, are constant in the object and the reception efficiency of the probes are same. In FIG. 5, ultrasonic probes or transducers A, B are disposed one on each side of a defect 2 in an object or tube 1 so that an ultrasonic beam emitted from the probe A will be transmitted through the defect 2 toward the probe B. Another ultrasonic probe or transducer C is positioned to receive an ultrasonic echo from the defect 2. The beam path from the probe A to the probe B has a length l and a central point D, and the beam path from the defect 2 to the probe C has a length l/2. The transmitted ultrasonic beam travels from the probe A to the probe B in the direction of the arrow RB, and the reflected ultrasonic echo travels from the probe A through the defect 2 to the probe C in the direction of the arrow RC, the reference characters RB, RC being hereinafter used as received sound pressures of ultrasonic energies which have travelled in those directions.

The porbes B, C thus located in FIG. 5 serve to measure transmitted and reflected amounts, i.e., transmitted and reflected sound pressures RB, RC, respectively, of ultrasonic energy emitted from the probe A, in any desired axial direction of the tube and around the entire circumferential surface thereof. The measured data is processed as follows:

The reflected and transmitted sound pressures RC, RB are expressed as follows:
$RC = P_o K \Gamma R e^{-\mu l}$
$RB = P_o K \Gamma T e^{-\mu l}$
where
RC: the reflected sound pressure,
RB: the transmitted sound pressure,
K: a coefficient relating to the reciprocal transmittion ratio at the tube surface and the spreading of the ultrasonic wave,
$\Gamma R$: a reflection coefficient, of the defect
$\Gamma T$: a transmittion ceofficient, of the defect
$\mu$: an attenuation coefficient,
l: the distance over which the ultrasonic energy is transmitted and reflected (beam path length),
Po: the sound pressure. transmitted by the probe A.
According to this embodiment, the respective measured values are related by the following evaluation formulas:

Evaluation value = $RC/RB = \Gamma R/\Gamma T =$ a constant dependent solely on the shape of the defect.

Figure 6:
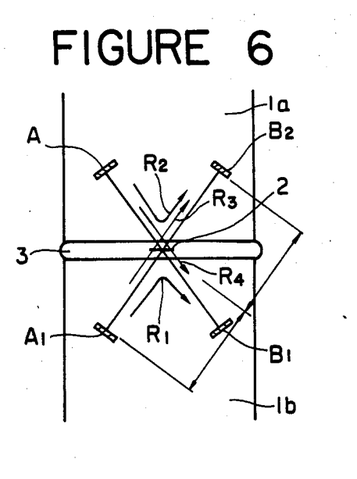
FIG. 6 is a view of an arrangement of four ultrasonic probes utilized in a method of a still further embodiment.

FIG. 6 shows another arrangement of ultrasonic probes or transducers according to a still further embodiment for a tube having tube portions 1a, 1b welded together by a weld seam 3 containing a defect 2 and having different material properties, the tube portions 1a, 1b having attenuation coefficients $\mu 1$, $\mu 2$, when others of influencing factors except for attenuation coefficient are constant in the object and the sound pressures transmitted by the probes, the transmittion efficiency and the reception efficiency are nearly same each other. Two transmitter probes A1, A2 and two receiver probes B1, B2 are disposed in conjugate relation with respect to an area to be inspected which contains the defect 2. The receiver probe B1 receives an ultrasonic echo R1 emitted from the transmitter probe A1 and reflected by the defect 2 and an ultrasonic beam R4 emitted from the transmitter probe A2 and transmitted through the defect 2. The receiver probe B2 receives an ultrasonic beam R3 emitted from the transmitter probe A1 and transmitted through the defect 2 and an ultrasonic echo R2 emitted from the transmitter probe A2 and reflected by the defect 2. The reference characters R1, R2, R3, R4 will also be used as denoting received sound pressures of these ultrasonic beams and echoes.

The received sound pressures are given as follows:
$R1 = P_0 \Gamma R K e^{-\mu 1 l}$
$R2 = P_0 \Gamma R K e^{-\mu 2 l}$
$R3 = P_0 \Gamma T k e^{-\mu 1 l/2} e^{-\mu 2 l/2}$
$R4 = P_0 \Gamma T K e^{-\mu 1 l/2} e^{-\mu 2 l/2}$ $$\text{Evaluation value} = R1 \times R2/R3 \times R4 = \frac{\Gamma R^2}{\Gamma T^2} =$$

a constant dependent solely on the shape of the defect.

The evluation value is effective in ascertaining whether there is a defect or not without dependency on the characteristics inherent in the materials having varying properties on both sides of the welded seam, resulting in highly reliable flaw detection.

Figure 7:
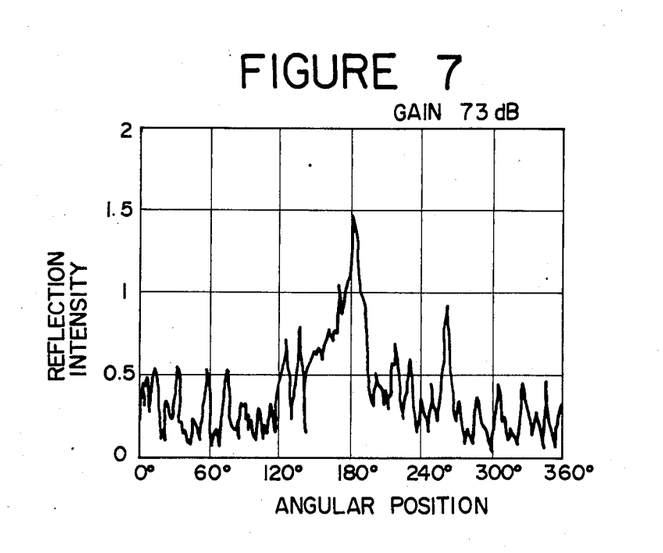
FIG. 7 is a graph showing the waveform of a reflected ultrasonic energy between a probe pair, dependent on the angular position around a tube being inspected.
Figure 8:
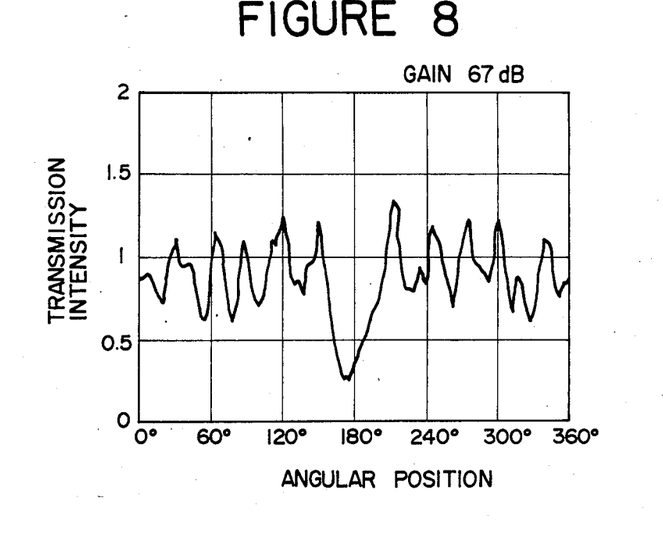
FIG. 8 is a graph showing the waveform of a transmitted ultrasonic energy between a probe pair, dependent on the angular position around a tube being inspected.

The data items are measured successively moving the probes fully around the tube. The measured data and their related results are as follows:

FIG. 7 is graph showing data obtained from reflected ultrasonic echoes detected by the probe arrangement shown in FIG. 5, the graph having a horizontal axis representing the angular position around the tube and a vertical axis the intensity of the reflected sound pressure. FIG. 8 is a graph showing data obtained simultaneously from transmitted ultrasonic echoes detected by the probe arrangement of FIG. 5, the graph having a horizontal axis representing the angular position around the tube and a vertical axis the intensity of the transmitted sound pressure. The tube tested had an artificial defect having a depth which is ½ of the wall thickness of the tube, the graphs of FIGS. 7 and 8 showing arrows indicating the position of the defect. Since the tube tested had simplified material properties and defect conditions, the waveforms shown in FIGS. 7 and 8 clearly show the defect among many echoes and transmitted sound pressures. With actual tubes manufactured in centrifugal casting, however, it would be quite difficult to identify the presence of a defect on the graphs.

Figure 9:
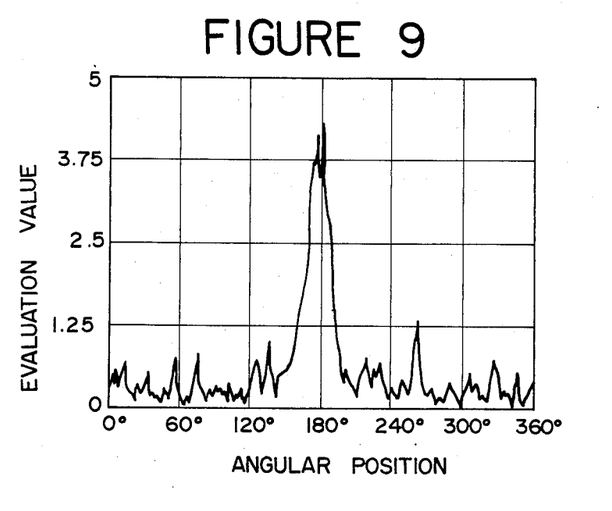
FIG. 9 is a graph representing evaluation values derived from the data produced by the probe arrangement of FIG. 5, dependent on the angular position around the tube.

FIG. 9 illustrates results computed from the evaluation value RC/RB according to the method of the invention. The graph of FIG. 9 has a vertical axis indicative of dimensionless values which are free from the influences of the tube material properties.

The same results as those shown in FIGS. 7 through 9 can be obtained by arranging the ultrasonic probes as illustrated in FIG. 6 and computing the evaluation value $R1 \times R2/R3 \times R4$ from the detected data.

Figure 10:
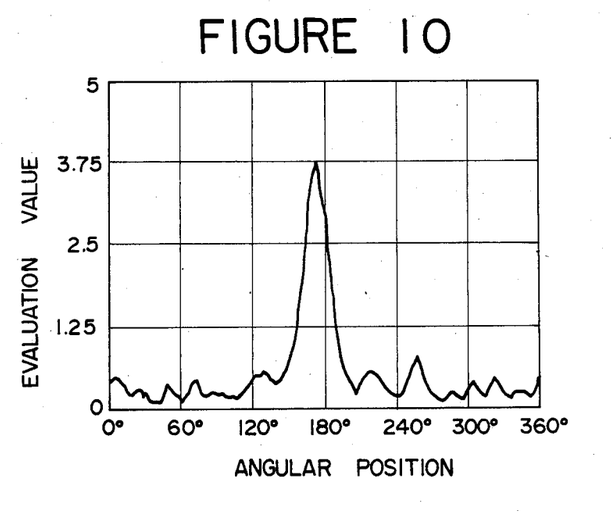
FIG. 10 is a graph similar to FIG. 9, showing evaluation values derived from the averaged data.

The transmitted and reflected ultrasonic waves are subject to locally scattered noises generated at grain boundaries, these noises being random noises which would vary in different beam paths. Since any defect or flaw has a certain spatial extent, ultrasonic energies reflected from or transmitted through the defect are spread in a certain angular interval around a tube being inspected. In view of the above difference between the locally scattered noises and the defect-induced ultrasonic energy levels, the data obtained in the circumferential and axial directions of the tube are averaged to produce secondary data in which the locally scattered noises are rendered flat relatively. The secondary data are then processed to produce an evaluation value according to the present invention. This process can detect flaws or deficiencies with higher reliability as shown in FIG. 10. Instead of averaging raw data and processing the average data, the raw data may first be processed to produce an evaluation value which may then be averaged.

Figure 11:
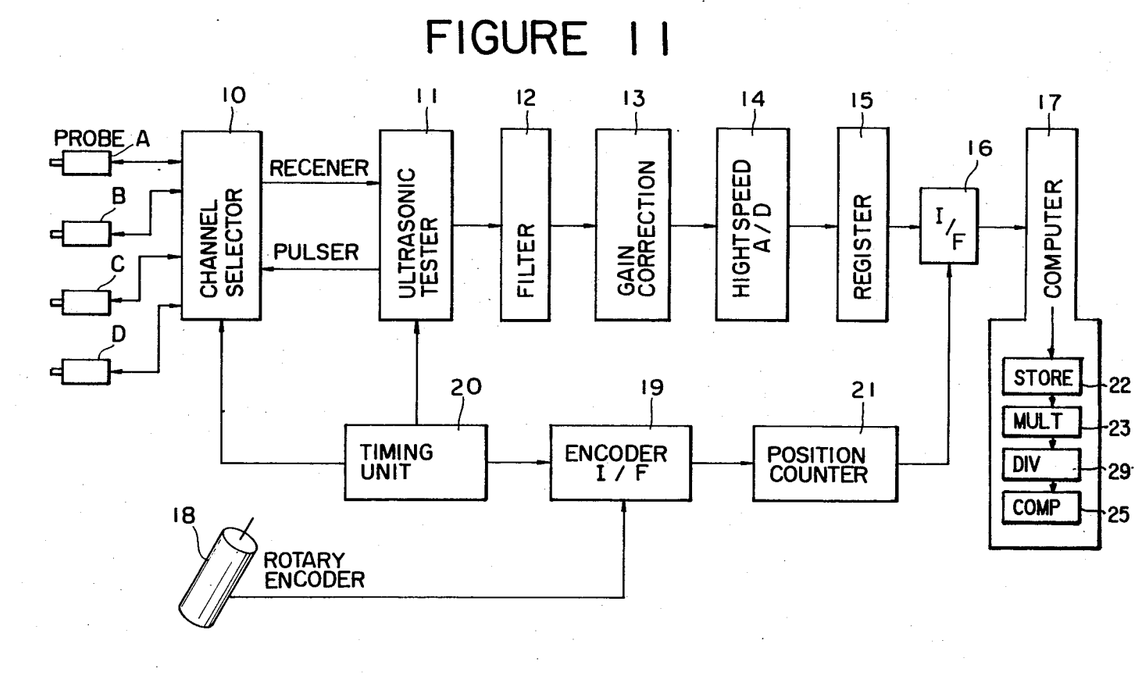
FIG. 11 a block diagram of a circuit arrangement for carrying out the method of the present invention.

FIG. 11 shows in block diagram a circuit arrangement for ultrasonically detecting a flaw in an object according to the present invention.

As shown in FIG. 11, a channel selector 10 is connected to four ultrasonic probes or transducers A, B, C, D which can emit an ultrasonic wave having a frequency ranging from 0.1 MHz to 10 MHz to an object such as a tube being tested and also can receive an ultrasonic wave reflected or transmitted from the tube and convert the same to an electric signal. The channel selector 10 selects one ultrasonic probe as an ultrasonic transmitter and another ultrasonic probe as an ultrasonic receiver. The channel selector 10 sequentially selects different transmitter/receiver pairs and connect them to an ultrasonic tester 11 which momemtarily applies a high voltage to the selected ultrasonic transmitter to enable it to emit an ultrasonic beam and also receives the electric signal from the selected ultrasonic receiver. The signal from the ultrasonic tester 11 is filtered by a filter 12 and the filtered signal is fed to a gain correction circuit 13. The signal corrected to a prescribed level is applied to a high-speed analog-to-digital (A/D) converter 14 which converts the signal to a digital signal. The digital signal from the high-speed A/D converter 14 is stored in a register 15. The stored signal is read through an interface 16 into a computer 17. The computer 17, which may be composed of a 16-bit CPU, serves to process the data obtained successively from the ultrasonic probes A, B, C, D into an evaluation value as described above in the methods of the present invention.

Computer 17 includes a storage device 22 for holding the signals read through the interface from the register. When the evaluation value is calculated, the appropriate storage signals are multiplied together in miltiplier circuit 23. The two products of the transmitted and reflected waves are then received by the divider circuit 24 in order to produce the evaluation value. This value is then compared to a fixed value in comparator 25.

The assembly of the probes A, B, C, D is coupled to a rotary encoder 18 which produces a signal indicative of the angular position of the probes with respect to the tube. The position signal from the encoder 18 is fed to an encoder interface 19 which generates a trigger signal. In response to the trigger signal from the encoder interface 19, a timing unit 20 issues a timing signal to the channel selector 10 and the ultrasonic tester 11 for enabling the latter to receive signals successively from the ultrasonic probes A, B, C, D. The trigger signal from the encoder interface 19 is also applied to a position counter 21 which counts the position of the probes with respect to the tube. The position counter 21 applies a signal to the interface 16.

Although certain preferred embodiments have been shown and described, it should be understood that many changes and modifications may be made therein without departing from the scope of the appended claims.

We claim:

1. A method of ultrasonically detecting a flaw in an object, comprising the steps of:
    (a) positioning a plurality of ultrasonic transducers around a region of the object to be inspected;
    (b) sequentially energizing more than one of said ultrasonic transducers to emit a series of ultrasonic beams into said region;
    (c) receiving ultrasonic waves reflected from and transmitted through said region in response to each emitted ultrasonic beam;
    (d) measuring sound pressures from the reflected and transmitted ultrasonic waves; and
    (e) producing an evaluation value by arithmetically dividing the product of the sound pressures of each reflected ultrasonic wave by the product of the sound pressures of each transmitted ultrasonic wave.

2. A method according to claim 1, wherein four ultrasonic transducers are disposed around said region in angularly spaced relation to each other, said four ultrasonic transducers being sequentially energized to emit ultrasonic beams, and two of said four ultrasonic transducers which are adjacent and diagonally opposite to the energized ultrasonic transducer being sequentially selected to recieve the reflected and transmitted ultrasonic waves, respectively.

3. A method according to claim 1, wherein two ultrasonic transducers are disposed one on each side of said region, said two ultrasonic transducers being alternately energized to emit ultrasonic beams and simultaneously operated to receive the reflected and transmitted ultrasonic waves, respectively.

4. A method according to claim 1, wherein four ultrasonic transducers are disposed around said region in angularly spaced relation to each other, two of said four ultrasonic transducers being alternately energized to emit ultrasonic beams, and the other two of said four ultrasonic transducers which are adjacent and diagonally opposite to the energized ultrasonic transducer being selected to receive the reflected and transmitted ultrasonic waves, respectively.

5. An apparatus for ultrasonically detecting a flaw in an object, comprising:
    (a) a plurality of ultrasonic transducers disposed movably with respect to the object for sequentially emitting ultrasonic waves to a region of the object to be inspected and for recieving ultrasonic waves reflected from and transmitted through said region and converting the received ultrasonic waves to electric signals;
    (b) an encoder coupled to said ultrasonic transducers for generating a positional signal indicating the position of said ultrasonic transducers with respect to said object;
    (c) an analog-to-digital converter for converting the received electric signals to digital signals;
    (d) a register for storing said digital signals; and
    (e) a computer for processing said digital signals from said register into an evaluation value by arithmetically dividing the product of the sound pressures of each reflected ultrasonic wave by the product of the sound pressures of each transmitted ultrasonic wave.

6. An apparatus according to claim 5, wherein said means comprises a channel selector for sequentially selecting one of said ultrasonic transducers as an ultrasonic transmitter for emitting the ultrasonic wave and two of said ultrasonic transducers as ultrasonic receivers for receiving the reflected and transmitted ultrasonic waves, and an ultrasonic tester for energizing the selected ultrasonic transmitter and receiving the electric signals from the selected ultrasonic receivers.

* * * * *